United States Patent
Ottoboni et al.

(10) Patent No.: US 6,193,951 B1
(45) Date of Patent: Feb. 27, 2001

(54) MICROPARTICLES USEFUL AS ULTRASONIC CONTRAST AGENTS

(75) Inventors: Thomas B. Ottoboni, Belmont; Robert E. Short, Los Gatos; Ronald K. Yamamoto, San Francisco, all of CA (US)

(73) Assignee: Point Biomedical Corporation, San Carlos, CA (US)

( * ) Notice: Subject to any disclaimer, the term of this patent is extended or adjusted under 35 U.S.C. 154(b) by 0 days.

(21) Appl. No.: 09/070,474

(22) Filed: Apr. 30, 1998

Related U.S. Application Data

(63) Continuation-in-part of application No. 08/847,153, filed on Apr. 30, 1997, now abandoned.

(51) Int. Cl.$^7$ ............................................. A61B 8/13
(52) U.S. Cl. ............................................. 424/9.5; 424/9.52
(58) Field of Search ........................... 424/9.5, 9.52; 600/431, 458

(56) References Cited

U.S. PATENT DOCUMENTS

| | | |
|---|---|---|
| 3,743,604 | 7/1973 | Schnoring et al. . |
| 4,718,433 | 1/1988 | Feinstein ........................ 424/9.52 |
| 5,041,292 | 8/1991 | Feijen ............................. 424/484 |
| 5,271,961 | 12/1993 | Mathiowitz et al. ........... 427/213.31 |
| 5,310,540 | 5/1994 | Giddey et al. ................. 424/9.52 |
| 5,387,221 | * | 2/1995 | Bernstein et al. .............. 424/9.52 |
| 5,501,863 | * | 3/1996 | Rossling et al. ............... 424/489 |
| 5,518,709 | 5/1996 | Sutton et al. . |
| 5,562,893 | * | 10/1996 | Lohrmann et al. ............ 424/9.52 |
| 5,569,468 | 10/1996 | Modi ............................. 424/491 |
| 5,611,344 | * | 3/1997 | Bernstein et al. ............. 128/662.02 |
| 5,620,883 | 4/1997 | Shao et al. . |
| 5,679,377 | 10/1997 | Bernstein et al. ............ 428/402.2 |
| 5,711,933 | * | 1/1998 | Bichon et al. ................. 424/9.52 |
| 5,840,275 | * | 11/1998 | Bichon et al. ................. 424/9.52 |
| 5,863,520 | * | 1/1999 | Bichon et al. ................. 424/9.52 |
| 5,919,434 | * | 7/1999 | Dugstad et al. ............... 424/9.52 |
| 5,922,304 | * | 7/1999 | Unger ............................ 424/9.3 |
| 5,948,387 | * | 9/1999 | Unger et al. .................. 424/9.5 |

FOREIGN PATENT DOCUMENTS

| | | |
|---|---|---|
| 0 224 934 B1 | 6/1987 | (EP) . |
| 0 441 468 B1 | 8/1991 | (EP) . |
| 458 745 A1 | 11/1991 | (EP) . |
| 0 512 693 A1 | 11/1992 | (EP) . |
| 0 681 843 A2 | 11/1995 | (EP) . |
| 2 256 183 | 12/1992 | (GB) . |
| WO 91/12823 | 9/1991 | (WO) . |
| WO 92/18164 | 10/1992 | (WO) . |

* cited by examiner

*Primary Examiner*—Gary E. Hollinden
(74) *Attorney, Agent, or Firm*—Fish & Richardson, PC

(57) ABSTRACT

Microparticles are provided comprising a shell of an outer layer of a biologically compatible material and an inner layer of biodegradable polymer. The core of the microparticles contain a gas, liquid or solid for use in drug delivery or as a contrast agent for ultrasonic contrast imaging. The microparticles are capable of passing through the capillary systems of a subject.

41 Claims, 2 Drawing Sheets

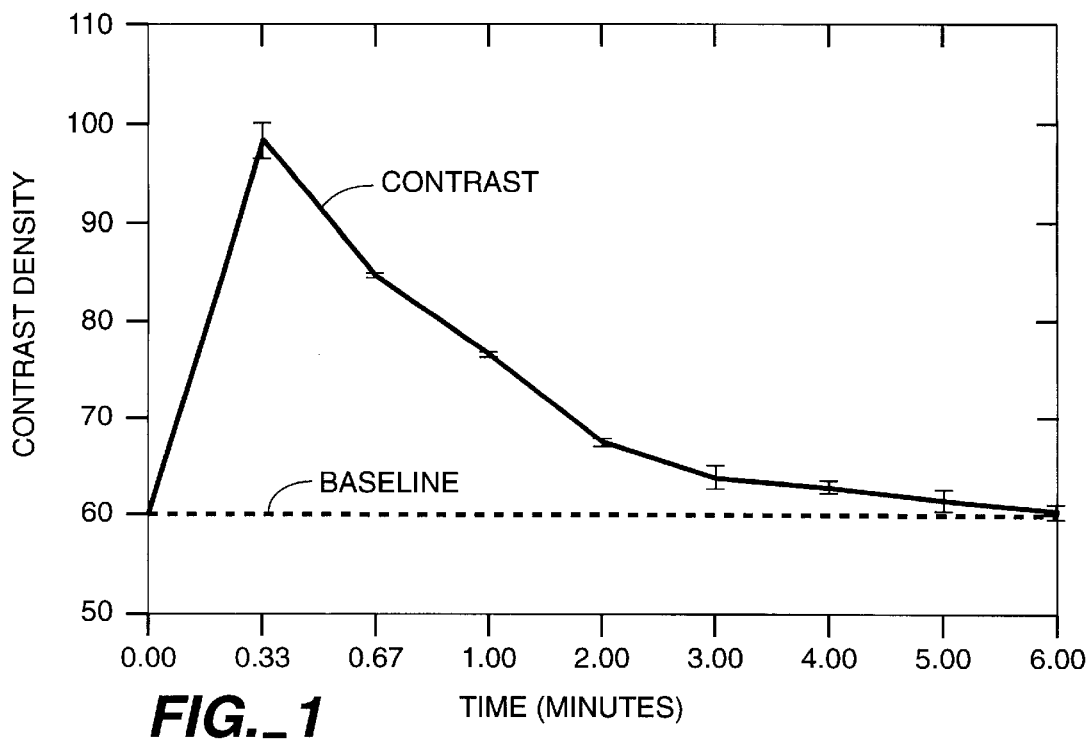
FIG._1
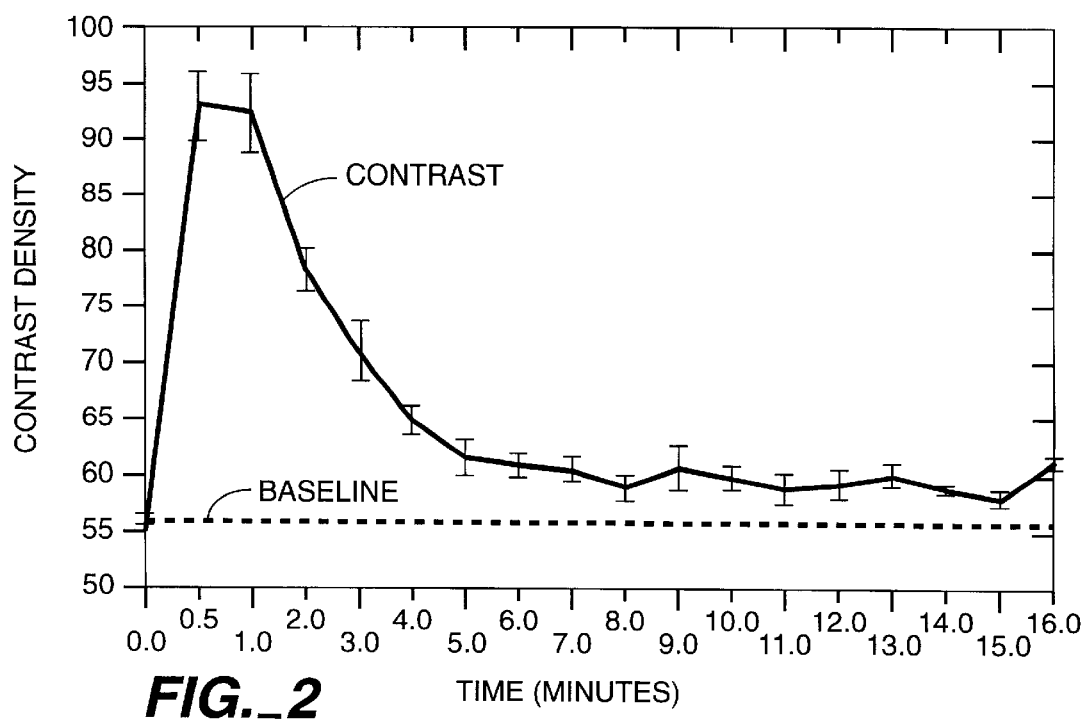
FIG._2

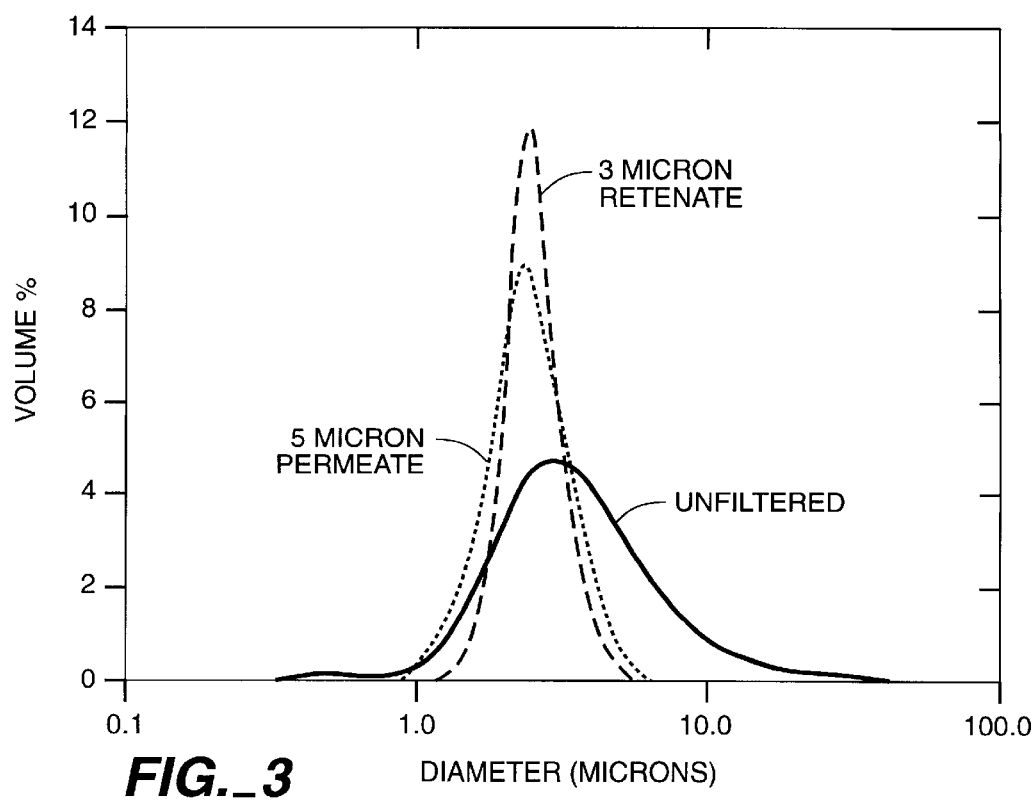
FIG._3
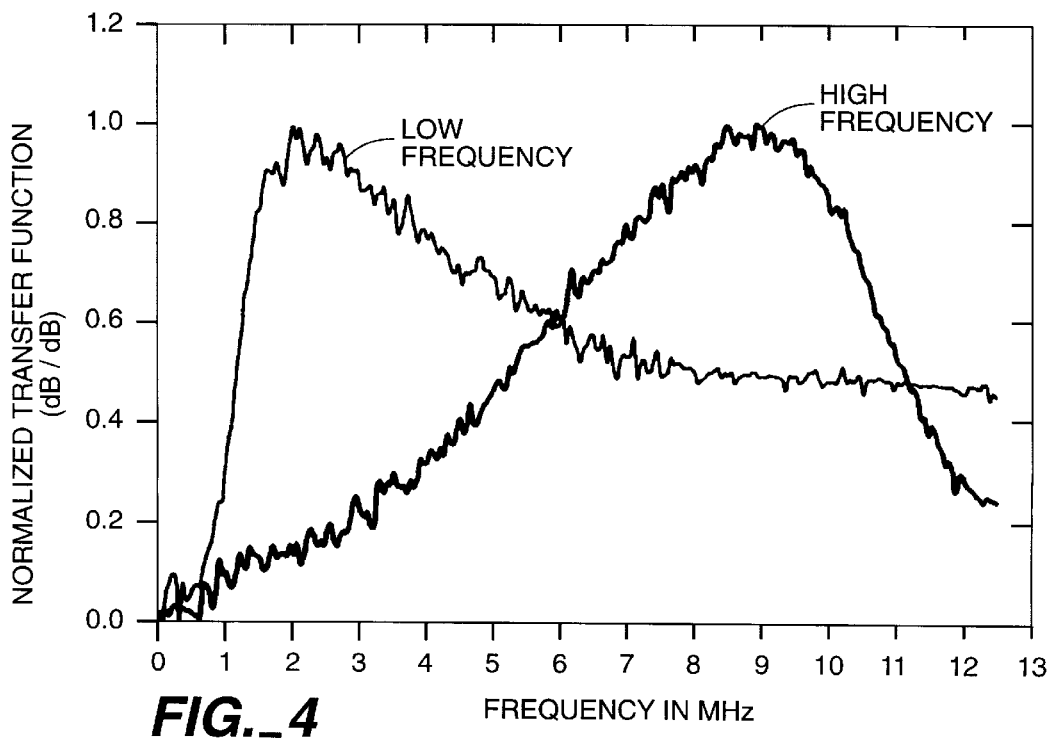
FIG._4

MICROPARTICLES USEFUL AS ULTRASONIC CONTRAST AGENTS

This is a continuation-in-part of Ser. No. 08/847,153, filed Apr. 30, 1997, abandoned incorporated by reference herein in its entirety.

BACKGROUND OF THE INVENTION

Hollow microparticles, sometimes called microbubbles or microspheres, are efficient for back scattering ultrasound energy. Thus, small microbubbles injected into the bloodstream, can enhance ultrasonic echographic imaging to aid the visualization of internal structures, such as the heart and blood vessels. The ultrasound contrast is achieved when acoustic impedance between two materials at an interface is different. Thus, the greater the difference of acoustic impedance between the materials, the greater the intensity of an ultrasound echo from that interface. Since there is a large difference between the acoustic impedance between body tissue and gas, gas containing microparticles circulating within tissue or blood are strong back scatterers of the ultrasound energy. For use in the circulatory system, microparticles should have a diameter of less than about ten microns in order to pass through the capillaries of the circulatory system. The lower limit of sufficient echogenicity of a microparticle is about one to two microns.

In cardiology, microparticles are useful for intravenous injection, thereby providing ultrasound contrast in the right chambers of the heart, enhancing identification of cardiac structures, valve functions and detection of intracardiac shunts. However, in order to visualize the left chambers of the heart, the microparticles must first pass through the pulmonary circulation system. Such particles must be small enough to pass through the pulmonary capillaries, otherwise they are trapped within the lungs. The particles must also have sufficient structural strength to survive the pressures within the left chambers of the heart.

Microparticles also permit the definition of volumes, wall motion, and other factors that identify diseased states within the heart. The use of contrast agents also facilitates use of Doppler ultrasound techniques because strong echo sources moving in the bloodstream are far more echogenic than red blood cells, which are the usual echo sources used in Doppler ultrasound techniques. Contrast agents in blood may also be used to locate the presence of blood in areas of the body or identify the absence of blood by the lack of echogenicity in areas that should be echogenic. Examples of such uses are the use of microparticles for assessment of perfusion to the myocardium, and for assessment of defects in the coronary septum by the flow of particles through the septum separating the cardiac chambers. Another example is the use of microparticles to identify vascular emboli such as blood clots, and abnormal growths into the vascular chambers by the absence of the ultrasonic contrast.

Other uses of contrast agents are to examine organ perfusion, such as to assess the damage caused by an infarct, to examine organs such as the liver, or to differentiate between normal and abnormal tissues, such as tumors and cysts.

The present invention provides microparticle contrast agents which are delivered intravenously but are capable of passing through the pulmonary circulation system for enhanced examination and diagnosis of both sides of the heart as well as examination of other tissues and organs as described above.

In addition to diagnostic imaging, the microparticles according to the present invention are also used for drug delivery where the drug is released from the particle by diffusion from the microparticle, by degradation of the microparticle, or by rupture of the particle using ultrasonic energy.

SUMMARY OF THE INVENTION

The present invention provides compositions of microparticles of which the majority of the microparticles have diameters within the range of about one to ten microns, have an outer layer comprising a biologically compatible material and an inner layer comprising a biodegradable polymer. The microparticles may have a hollow core, containing either a gas or a liquid, or a solid core.

The outer layer may be chosen on the basis of biocompatibility with the blood stream and tissues, whereas the inner layer may be selected on the basis desired mechanical and acoustic properties. The materials of both layers may be selected to predetermine the strength of the microparticle, for example to provide a desired resonant frequency and stability within threshold diagnostic imaging levels of ultrasound radiation. Methods for forming the multi-layered microparticles and the use in ultrasonic diagnostic imaging and drug delivery are also provided. The layers may also be chosen by their capability to contain and deliver drugs.

BRIEF DESCRIPTION OF THE DRAWINGS

FIG. 1 is a graph of the time course of the reflected ultrasound intensity in the left atrium in a test of a contrast agent according to example 7.

FIG. 2 is a graph of the time course of the reflected ultrasound intensity in the left atrium of the contrast agent tested in accordance with example 8.

FIG. 3 is a graph of the volumetric size distribution of the unfiltered microcapsules made in example 13, and the size distribution of when the suspension is filtered.

FIG. 4 shows the resonant frequencies of two microcapsule preparations having different wall compositions which were tested in accordance with example 18.

DESCRIPTION OF THE PREFERRED EMBODIMENTS

As used herein the term microparticles is intended to include microcapsules, microspheres and microbubbles which are hollow particles enclosing a core which may be filled with a gas or liquid. It also includes particles in which the core may be a solid material. It is not necessary for the microparticles to be precisely spherical although they generally will be spherical and described as having average diameters. If the microparticles are not spherical, then the diameters are referred to or linked to the diameter of a corresponding spherical microparticle having the same mass and enclosing approximately the same volume of interior space as a non-spherical microparticle.

The microparticles according to the present invention have a bi-layered shell. The outer layer of the shell will be a biologically compatible material or biomaterial since it defines the surface which will be exposed to the blood and tissues within the body. The inner layer of the shell will be a biodegradable polymer, which may be a synthetic polymer, which may be tailored to provide the desired mechanical and acoustic properties to the shell or provide drug delivery properties. For use as ultrasound contrast agents, the cores of the microparticles contain gas, typically air or nitrogen. However, for drug delivery purposes the core may either be a liquid or a different solid material from the shell layers. To make the microparticles rupturable by a low intensity ultrasound energy, however, they must contain a gas to allow acoustic coupling and particle oscillation. Microparticles are constructed herein such that the majority of those prepared in a composition will have diameters within the range of about one to ten microns in order to pass through the capillary system of the body.

Since the microparticles have an outer and inner layer, the layers can be tailored to serve different functions. The outer shell which is exposed to the blood and tissues serves as the biological interface between the microparticles and the body. Thus it will be made of a biocompatible material which is typically amphiphilic, that is, has both hydrophobic and hydrophilic characteristics. Blood compatible materials are particularly preferred. Such preferred materials are biological materials including proteins such as collagen, gelatin or serum albumins or globulins, either derived from humans or having a structure similar to the human protein, glycosoaminoglycans such as hyaluronic acid, heparin and chondroiten sulphate and combinations or derivatives thereof. Synthetic biodegradable polymers, such as polyethylene glycol, polyethylene oxide, polypropylene glycol and combinations or derivatives may also be used. The outer layer is typically amphiphilic, as well as having a chemistry which allows charge and chemical modification. The versatility of the surface allows for such modifications as altering the charge of the outer shell, such as by selecting a type A gelatin having an isoelectric point above physiological pH, or by using a type B gelatin having an isoelectric point below physiological pH. The outer surfaces may also be chemically modified to enhance biocompatibility, such as by PEGylation, succinylation or amidation, as well as being chemically binding to the surface targeting moiety for binding to selected tissues. The targeting moieties may be antibodies, cell receptors, lectins, selecting, integrins or chemical structures or analogues of the receptor targets of such materials. The mechanical properties of the outer layer may also be modified, such as by cross linking, to make the microparticles suitable for passage to the left ventricle, to provide a particular resonant frequency for a selected harmonic of the diagnostic imaging system, or to provide stability to a threshold diagnostic imaging level of the ultrasound radiation.

The inner shell will be a biodegradable polymer, which may be a synthetic polymer. An advantage of the inner shell is that it provides additional mechanical or drug delivery properties to the microparticle which are not provided or insufficiently provided by the outer layer, or enhances mechanical properties not sufficiently provided by the outer layer, without being constrained by surface property requirements. For example, a biocompatible outer layer of a cross-linked proteinaceous hydrogel can be physically supported using a high modulus synthetic polymer as the inner layer. The polymer may be selected for its modulus of elasticity and elongation, which define the desired mechanical properties. Typical biodegradable polymers include polycaprolactone, polylactic acid, polylactic-polyglycolic acid co-polymers, co-polymers of lactides and lactones, such as epsilon-caprolactone, delta-valerolactone, polyalkylcyanoacrylates, polyamides, polyhydroxybutryrates, polydioxanones, poly-beta-aminoketones, polyanhydrides, poly-(ortho)esters, polyamino acids, such as polyglutamic and polyaspartic acids or esters of polyglutamic and polyaspartic acids. References on many biodegradable polymers are cited in Langer, et. al. (1983) *Macromol.Chem.Phys.*C23, 61–125.

The inner layer permits the modification of the mechanical properties of the shell of the microparticle which are not provided by the outer layer alone. Moreover, the inner layer may provide a drug carrier and/or drug delivery capacity which is not sufficient or providable by the outer layer alone. For use as an ultrasonic contrast agent, the inner layer will typically have thickness which is no larger than is necessary to meet the minimum mechanical or drug carrying/delivering properties, in order to maximize the interior gas volume of the microparticle. The greater the gas volume within the microparticle the better the echogenic properties.

The combined thickness of the outer and inner layers of the microparticle shell will depend in part on the mechanical and drug carrying/delivering properties required of the microparticle, but typically the total shell thickness will be in the range of 25 to 750 nm.

The microparticles may be prepared by an emulsification process to control the sequential interfacial deposition of shell materials. Due to the amphiphilicity of the material forming the outer layer, stable oil/water emulsions may be prepared having an inner phase to outer phase ratio approaching 3:1, without phase inversion, which can be dispersable in water to form stable organic phase droplets without the need for surfactants, viscosity enhancers or high shear rates.

Two solutions are prepared, the first being an aqueous solution of the outer biomaterial. The second is a solution of the polymer which is used to form the inner layer, in a relatively volatile water-immiscible liquid which is a solvent for the polymer, and a relatively non-volatile water-immiscible liquid which is a non-solvent for the polymer. The relatively volatile water-immiscible solvent is typically a C5–C7 ester, such as isopropyl acetate. The relatively non-volatile water-immiscible non-solvent is typically a C6–C20 hydrocarbon such as decane, undecane, cyclohexane, cyclooctane and the like. In the second solution containing the polymer for the inner layer, the polymer in water-immiscible solvents are combined so that the polymer fully dissolves and the two solvents are miscible with agitation. The polymer solution (organic phase) is slowly added to the biomaterial solution (aqueous phase) to form a liquid foam. Typically about three parts of the organic polymer solution having a concentration of about 0.5 to 10 percent of the polymer is added to one part of the aqueous biomaterial solution having a concentration of about 1 to 20 percent of the biomaterial. The relative concentrations of the solutions and the ratio of organic phase to aqueous phase utilized in this step essentially determine the size of the final microparticle and wall thickness. After thorough mixing of the liquid foam, it is dispersed into water and typically warmed to about 30–35° C. with mild agitation. While not intending to be bound by a particular theory, it is believed that the biomaterial in the foam disperses into the warm water to stabilize an emulsion of the polymer in the organic phase encapsulated within a biomaterial envelope. To render the biomaterial envelope water insoluble, a cross linking agent, such as glutaraldehyde, is added to the mixture to react with the biomaterial envelope and render it water insoluble, stabilizing the outer shell. Other cross-linking agents may be used, including the use of carbodiimide cross-linkers.

Since at this point the inner core contains a solution of a polymer, a solvent and a non-solvent with different volatilities, as the more volatile solvent evaporates, or is diluted, the polymer precipitates in the presence of the less volatile non-solvent. This process forms a film of precipitate at the interface with the inner surface of the biomaterial shell, thus forming the inner shell of the microparticle after the more volatile solvent has been reduced in concentration either by dilution, evaporation or the like. The core of the microparticle then contains predominately the organic non-solvent. The microparticles may then be isolated by centrifugation, washed, formulated in a buffer system, if desired, and dried. Typically, drying by lyophilization removes not only the non-solvent liquid core but also the residual water to yield gas-filled hollow microparticles.

It may be desirable to further modify the surface of the microparticle, for example, in order to passivate surfaces against macrophages or the reticuloendothelial system (RES) in the liver. This may be accomplished, for example by chemically modifying the surface of the microparticle to be negatively charged since negatively charged particles appear to better evade recognition by macrophages and the RES than positively charged particles. Also, the hydrophilicity of the surface may be changed by attaching hydrophilic conjugates, such as polyethylene glycol (PEGylation) or succinic acid (succinylation) to the surface, either alone or in conjunction with the charge modification.

The biomaterial surface may also be modified to provide targeting characteristics for the microparticle. The surface may be tagged by known methods with antibodies or biological receptors. For example, if the microparticle were treated to target tumors and were hollow, they could be used for ultrasound detection to enhance diagnosis of the tumors. If the microparticles were filled with drugs they could be used to target the tumors where the drug could be preferentially released at the target site, for example, by increasing the ultrasonic energy to rupture the particles at the appropriate time and location.

The microparticles may also be sized or processed after manufacture. This is an advantage over lipid-like microparticles which may not be subjected to mechanical processing after they are formed due to their fragility.

The final formulation of the microparticles after preparation, but prior to use, is in the form of a lyophilized cake. The later reconstitution of the microparticles may be facilitated by lyophilization with bulking agents which provide a cake having a high porosity and surface area. The bulking agents may also increase the drying rate during lyophilization by providing channels for the water and solvent vapor to be removed. This also provides a higher surface area which would assist in the later reconstitution. Typical bulking agents are sugars such as dextrose, mannitol, sorbitol and sucrose, and polymers such as PEG's and PVP's.

It is undesirable for the microparticles to aggregate, either during formulation or during later reconstitution of the lyophilized material. Aggregation may be minimized by maintaining a pH of at least one to two pH units above or below the isoelectric point($P_i$) of the biomaterial forming the outer surface. The charge on the surface is determined by the pH of the formulation medium. Thus, for example, if the surface of the biomaterial has a $P_i$ of 7 and the pH of the formulation medium is below 7, the microparticle will possess a net positive surface charge. Alternatively, if the pH of the formulation medium is greater than 7, the microparticle would possess a negative charge. The maximum potential for aggregation exist when the pH of the formulation medium approaches the $P_i$ of the biomaterial used in the outer shell. Therefore by maintaining a pH of the formulation medium at least one to two units above or below the $P_i$ of the surface, microparticle aggregation will be minimized. As an alternative, the microparticles may be formulated at or near the $P_i$ with the use of surfactants to stabilize against aggregation. In any event, buffer systems of the final formulation to be injected into the subject should be physiologically compatible.

The bulking agents utilized during lyophilization of the microparticles may also be used to control the osmolality of the final formulation for injection. An osmolality other than physiological osmolality may be desirable during the lyophilization to minimize aggregation. However, when formulating the microparticles for use, the volume of liquid used to reconstitute the microparticles must take this into account.

Other additives may be included in order to prevent aggregation or to facilitate dispersion of the microparticles upon formulation. Surfactants may be used in the formulation such as poloxomers (polyethylene glycol-polypropylene glycol-polyethylene glycol block co-polymers). Water soluble polymers also may assist in the dispersion of the microparticles, such as medium molecular weight polyethyleneglycols and low to medium molecular weight polyvinylpyrolidones.

If the formulation is to contain a drug-containing core, the microparticles may be soaked in a solution of the drug whereby the solution diffuses into the interior. In particular, the use of bilayered microparticles where the inner shell has a porous characteristic allows for rapid diffusion of a drug solution into the hollow core. The microparticles may be re-dried such as by lyophilization to produce a gas filled, drug containing microparticle. The combination of the drug with prefabricated particles allows one to avoid processing which may lead to drug degradation. To provide microparticles having a solid core containing a drug, during formation of the microparticles, the thickness of the inner layers may be increased to occupy more or all of the interior volume. Then, by later soaking in the drug-containing solution, the inner solid core will absorb the drug and provide a solid reservoir for the drug. Alternatively, the drug may be dissolved in the organic phase with the biopolymer during the microparticle forming process. Evaporation of the organic solvents causes the drug to coprecipitate with the biopolymer inside the microparticle.

It will be realized that various modifications of the above-described processes may be provided without departing from the spirit and scope of the invention. For example, the wall thickness of both the outer and inner layers may be adjusted by varying the concentration of the components in the microparticle-forming solutions. The mechanical properties of the microparticles may be controlled, not only by the total wall thickness and thicknesses of the respective layers, but also by selection of materials used in each of the layers by their modulus of elasticity and elongation, and degree of cross-linking of the layers. Upon certain conditions involving rapid deposition of the inner polymer or very low inner polymer content porosity of the inner polymer shell is observed. The pores range from approximately 0.1 to 2 micron in diameter as observed under electron microscopy. Mechanical properties of the layers may also be modified with plasticizers or other additives. Adjustment of the strength of the shell may be modified, for example, by the internal pressure within the microparticles. Precise acoustical characteristics of the microparticle may be achieved by control of the shell mechanical properties, thickness, as well as narrow size distribution. The microparticles may be ruptured by ultrasonic energy to release gases trapped within the microparticles into the blood stream. In particular, by appropriately adjusting the mechanical properties, the particles may be made to remain stable to threshold diagnostic imaging power, while being rupturable by an increase in power and/or by being exposed to its resonant frequency. The resonant frequency can be made to be within the range of transmitted frequencies of diagnostic body imaging systems or can be a harmonic of such frequencies. During the formulation process the microparticles may be prepared to contain various gases, including blood soluble or blood insoluble gases. It is a feature of the invention that microparticle compositions may be made having a resonant frequency greater or equal to 2 MHz, and typically greater or equal to 5 MHz.

Typical diagnostic or therapeutic targets for microparticles of the invention are the heart and tumors.

The following examples are provided by way of illustration but are not intended to limit the invention in any way.

EXAMPLE 1

Preparation of Gelatin Polycaprolactone Microparticles

A solution of 1.0 gms gelatin (275 bl, isoelectric point of 4.89) dissolved in 20 ml deionized water was prepared at approximately 60 C. Native pH of the solution was 5.07. Separately, 1.0 gms polycaprolactone (M.W. 50,000) and 6.75 ml cyclooctane was dissolved in 42 ml isopropyl acetate with stirring at approximately 70 C. After cooling to 37 C, the organic mixture was then slowly incorporated into the gelatin solution maintained at 30 C and under moderate shear mixing using a rotary mixer. Once the organic phase was fully incorporated, the mixing rate was increased to 2,500 rpm for 5 minutes and then stirred at low shear for an additional 5 minutes. The resulting o-w emulsion was then added with stirring to 350 ml deionized water maintained at 30 C and containing 1.2 ml 25% gluteraldehyde. Immediately after the addition of the emulsion, the bath pH was adjusted to 4.7. After 30 minutes, the pH was adjusted to 8.3. Low shear mixing was continued for approximately 2½ hours until the isopropyl acetate had completely volatilized. Polyoxamer 188 in the amount of 0.75 gm was then dissolved into the bath. The resulting microparticles were retrieved by centrifugation and washed 2 times in an aqueous solution of 0.25% polyoxamer 188.

Microscopic inspection of the microparticles revealed spherical capsules having a thin-walled polymer shell encapsulating a liquid organic core. Staining the slide preparation with coomassie blue G indicated the presence of an outer protein layer uniformly surrounding the polymer shell.

The particle size spectrum was determined using a Malvern Micro. Median diameter was 4.78 microns with a spectrum span of 0.94.

EXAMPLE 2

Preparation of Contrast Agent Formulation

A quantity of microparticles prepared in a manner similar to example 1 were suspended into an aqueous solution of 25 mM glycine, 0.5% pluronic f-127, 1.0% sucrose, 3.0% mannitol, and 5.0% PEG-3400. The suspension was then lyophilized. The resulting dry powder was reconstituted in deionized water and examined under the microscope to reveal that the microparticles now contained a gaseous core. Staining the preparation with commassie blue G confirmed that the outer protein layer surrounding the capsules was intact and had survived the lyophilization process.

Echogenicity was confirmed by insonating at both 2½ and 5 MHz a quantity of lyophilized microparticles dispersed in 120 ml deionized water. Measurement was taken at least 15 minutes after dispersion of the microcapsules to insure that the back scattered signal was due solely from the gas contained within the microparticles. The B mode display showed a high contrast indicating that the microparticles were gas filled.

EXAMPLE 3

Preparation of Gelatin Polylactide Microparticles

A solution of 1.2 gm gelatin (225 bloom, isoelectric point of 5.1) dissolved in 20 ml deionized water was prepared at approximately 50 C. Solution pH was adjusted to 6.1 using 1 M NaOH. Separately, 0.07 gms paraffin, 4.5 ml decane, and 0.69 gms poly DL-lactide (inherent viscosity of 0.69 dL/gm in $CHCl_2$ @ 30 C) was dissolved into 37 ml isopropyl acetate. The organic mixture was then slowly incorporated into the gelatin solution which was being maintained at 30 C under moderate shear mixing using a rotary mixer. Once the organic phase was fully incorporated, the mixing rate was increased to 2,000 rpm for 2 minutes and then reduced to approximately 1,000 rpm for 4 minutes. The resulting liquid foam was mixed into 350 ml deionized water maintained at 30 C and 1 ml 25% gluteraldehyde was then added dropwise. Rotary mixing was continued for approximately 3 hours until the isopropyl acetate had volatilized. The resulting microparticles were retrieved by centrifugation and washed 2 times in an aqueous solution of 0.25% pluronic f-127.

Microscopic inspection revealed hollow spherical microparticles having an outer protein layer and an inner organic liquid core.

The microparticles were lyophilized and tested in a manner similar to example 2. The results confirmed that the microparticles contained a gaseous core and were strongly echogenic.

EXAMPLE 4

Preparation of Gelatin Polycaprolactone Microparticles

A solution of 1.0 gm gelatin (225 bloom, isoelectric point of 5.1) dissolved in 20 ml deionized water was prepared at approximately 60 C. Solution pH was 4.8. Separately, 0.57 gms polycaprolactone (M.W. 50,000) was dissolved into 1.72 ml tetrahydrofuran. To this was added with stirring a mixture of 0.07 gms paraffin, 0.475 gm triethyl citrate, 4.5 ml cyclooctane, and 42 ml isopropyl acetate. The organic mixture was then slowly incorporated into the gelatin solution which was maintained at 30 C and under moderate shear mixing using a rotary mixer. Once the organic phase was fully incorporated, the mixing rate was increased to 4,700 rpm for 2 minutes and then reduced to 2,000 rpm for 4 minutes. The resulting liquid foam was then added with stirring to 350 ml of 30 C deionized water. To crosslink the gelatin, 1 ml of 25% glutaraldehyde was added dropwise. Mixing was continued for approximately 3 hours until the isopropyl acetate had volatilized. The resulting microparticles were retrieved by centrifugation and washed 2 times in a 0.25% pluronic f-127 solution.

Microscopic inspection revealed discrete hollow spherical polymer microparticles having an outer protein layer and an inner organic liquid core.

The microparticles were lyophilized and tested in a manner similar to example 2. The results confirmed that the microparticles contained a gaseous core and were strongly echogenic.

EXAMPLE 5

Preparation of Gelatin Polycaprolactone Microparticles with Cardodiimide Cross-linking A solution of 1.0 grams gelatin (225 bloom, isoelectric point of 5.1) dissolved into 20 ml deionized water was prepared at approximately 60 C. Solution pH was adjusted to 5.5 with 1 M NaOH. Separately, 0.85 gms polycaprolactone (M.W. 80,000) was dissolved in 2.5 ml tetrahydrofuran. To this was added with stirring a mixture of 0.07 gms paraffin, 4.5 ml cyclooctane and 42 ml isopropyl acetate. The organic mixture was then slowly incorporated into the gelatin solution which was maintained at 30 C and under moderate shear mixing using a rotary mixer. Once the organic phase was fully incorporated, the mixing rate was increased to 3,500 rpm for 6 minutes and then reduced to 3,000 rpm for 4 minutes. The resulting liquid foam was then dispersed with low shear mixing into 350 ml of a 0.5 M NaCl solution maintained at 30 C. Gelatin crosslinking was accomplished by the slow addition of 200 mg of 1-ethyl-3-(3-dimethylamino-propyl)carbodiimide dissolved in 3.0 ml deionized water. Mixing was continued for approximately 3 hours until the isopropyl acetate had volatilized. The resulting microparticles were retrieved by centrifugation and washed 2 times in an aqueous solution of 0.25% Pluronic f-127.

Microscopic inspection revealed discrete hollow spherical polymer microparticles having an outer protein layer and an inner organic liquid core.

EXAMPLE 6

Preparation of Surface PEGylated Microparticles

Microcapsules were prepared in a manner similar to example 1. After centrifugation the cream (approximately 15 ml) was retrieved and dispersed into a solution of 65 ml deionized water, 0.50 gms methoxy-PEG-NCO (M.W. 5000), and 0.50 ml triethylamine. After allowing the mixture to react overnight at room temperature and with mild agitation, the capsules were retrieved by centrifugation and washed 3 times in a neutrally buffered solution of 0.25% Pluronic f-127.

EXAMPLE 7

Canine Study of Echogenicity

One vial of lyophilized microparticles prepared in Example 2 were reconstituted using water. A transesophageal ultrasound probe was positioned in the esophagus of an anesthetized dog such that a four-chamber view of the heart was obtained. The microparticle suspension was injected into the femoral vein of the dog. The appearance of the contrast agent was clearly noted in the ultrasound image of the right chambers of the heart. Subsequently, the agent was observed in the left chambers of the heart indicating the passage through the capillary system of the lungs. The time-course of the reflected ultrasound intensity in the left atrium was determined by video densitometry. The agent was seen to persist in the left chambers of the heart for approximately 6 minutes (FIG. 1).

EXAMPLE 8

Canine Study of Echogenicity Using PEGylated Microparticles

One vial of lyophilized microparticles prepared in Example 6 was reconstituted using water. A transesophageal ultrasound probe was positioned in the esophagus of an anesthetized dog such that a four-chamber view of the heart was obtained. The microparticle suspension was injected into the femoral vein of the dog. The appearance of the contrast agent was clearly noted in the ultrasound image of the right chambers of the heart. Subsequently, the agent was observed in the left chambers of the heart indicating the passage through the capillary system of the lungs. The time-course of the reflected ultrasound intensity in the left atrium was determined by -video densitometry. The agent was seen to persist in the left chambers of the heart for approximately 16 minutes (FIG. 2) after which time no further data was collected.

EXAMPLE 9

Preparation of Albumin Polycaprolactone Microparticles

A 6% aqueous solution was prepared from a 25% solution of USP grade human serum albumin (Alpha Therapeutic Corp) by dilution with deionized water. The solution was adjusted to a pH of 3.49 using 1 N HCl. Separately, 8 parts by weight polycaprolactone (M.W. 50,000) and 45 parts cyclooctane were dissolved in 300 parts isopropyl acetate at approximately 70 C. Once dissolution was complete, the organic solution was allowed to cool to 37 C. With mild stirring, 42.5 gm of the prepared organic solution was slowly incorporated into 25.0 gm of the albumin solution while the mixture was maintained at 30 C. The resulting coarse o-w emulsion was then circulated through a stainless steel sintered metal filter element having a nominal pore size of 7 microns. Recirculation of the emulsion was continued for 8 minutes. The emulsion was then added with stirring to 350 ml deionized water maintained at 30 C and containing 1.0 ml of 25% gluteraldehyde. During the addition, the pH of the bath was monitored to insure that it remained between 7 and 8. Final pH was 7.1. Low shear mixing was continued for approximately 2½ hours until the isopropyl acetate had completely volatilized. Poloxamer 188 in the amount of 0.75 gm was then dissolved into the bath. The resulting microparticles were retrieved by centrifugation and washed 2 times in an aqueous solution of 0.25% poloxamer.

Microscopic inspection of the suspension revealed spherical particles having a thin-walled polymer shell with an outer protein layer and an organic liquid core. The peak diameter as, determined by the Malvern Micro particle size analyzer, was 4.12 microns.

The suspension was then lyophilized in a manner similar to that described in Example 2. The resulting dry cake was reconstituted with deionized water and examined under the microscope to reveal that the microparticles were spherical, discrete, and contained a gaseous core.

EXAMPLE 10

Protein Content of Microparticles

Microparticles were prepared in accordance with example 9. After centrifugation approximately 1 ml of the microparticle containing cream was retrieved and diluted 10 to 1 using deionized water. From the diluted cream, 20 microliter samples were then prepared in triplicate at 1x, 2x, and 4x dilutions with deionized water. Protein content of the samples were determined using a Pierce calorimetric BCA assay and a bovine serum albumin standard. Average total protein of the diluted cream was determined to be 0.441 mg/ml. To determine the total dry weight of the diluted cream, 2 ml were dried in a 40 C oven until no further weight change was observed (approximately 16 hours). The average weight of 4 replicates was 6.45 mg/ml. The percent dry weight of protein which can be used as a measure of the ratio of the protein outer layer to the polymer inner layer of the microcapsule wall can be determined with the following formula.

Average total protein/ml÷dry weight/ml×100%

The percent dry weight of protein was calculated to be 6.8%.

EXAMPLE 11

Preparation of Albumin Polylactide Microparticles

A 6% aqueous solution was prepared from a 25% solution of USP grade human albumin by dilution with deionized water. Ion exchange resin ( AG 501-X8, BioRad Laboratories) was then added to the solution at a ratio of 1.5 gm resin to 1.0 gm dry weight of albumin. After 3 hours the resin was removed by filtration and the pH of the solution was adjusted from 4.65 to 5.5 Separately, 0.41 gm d-1 lactide (0.69 dL/gm in $CHCl_3$: at 30 C) and 5.63 gm cyclooctane were dissolved in 37.5 gm isopropyl acetate. The organic solution was then slowly incorporated into 25.0 gm of the prepared albumin solution with mild stirring while the mixture was maintained at 30 C. The resulting coarse o-w emulsion was then circulated through a stainless steel sintered metal filter element having a nominal pore size of 7 microns. Recirculation of the emulsion was continued for 8 minutes. The emulsion was then added with stirring to 350 ml deionized water maintained at 30 C and containing 1.0 ml of 25% gluteraldehyde. During the addition, the pH of the bath was monitored to insure that it remained between 7 and 8. Final pH was 7.0. Low shear mixing was continued for approximately 2½ hours until the isopropyl acetate had completely volatilized. Polyoxamer 188 in the amount of 0.75 gm was then dissolved into the bath. The resulting microspheres were retrieved by centrifugation and washed 2 times in an aqueous solution of 0.25% polyoxamer.

Microscopic inspection revealed hollow spherical polymer microparticles having an outer protein layer and an inner organic liquid core. The suspension was formulated with a glycine/PEG 3350 excipient solution, then lyophilized. The resulting dry cake was reconstituted with deionized water and examined under the microscope to reveal that the microparticles were spherical, discrete, and contained a gaseous core.

EXAMPLE 12

PEG Modification of the Microparticle Surface

Microparticles were prepared in a manner similar to example 9. After centrifugation, 4 ml of the microparticles containing cream (approximately 11 ml total yield) was resuspended in 31 ml deionized water. To this was added a 10 ml solution containing 0.3 gm methoxy-peg-NCO 5000 and the pH was adjusted to 8.7. The mixture was allowed to react at room temperature with mild agitation for 4½ hours. At the end of this period the pH was measured to be 7.9. The microparticles were retrieved by centrifugation and washed 2 times in a 0.25% solution of polyoxamer 188. The suspension was formulated with a glycine/PEG 3350 excipient solution, then lyophilized. The resulting dry cake was reconstituted with deionized water and examined under the microscope to reveal that the microparticles were spherical, discrete, and contained a gaseous core.

EXAMPLE 13

Post-fabrication, Modification of Size Distribution

A quantity of microparticles were first prepared in a manner similar to example 1 with procedures modified to provide a broadened size spectrum. After washing and retrieval by centrifugation roughly half the microparticle containing cream was diluted to 125 ml with a 0.25% solution of polyoxamer 188. The suspension was then filtered using a 5 micron sieve type pc membrane filter (Nuclepore) housed in a stirred cell (Amicon). The retentate was discarded while the permeate was again filtered using a 3 micron sieve type filter in the stirred cell system until the retentate volume reached approximately 20 ml. The retentate was diluted to a volume of 220 ml using 0.25% polyoxamer 188 solution. The 3 micron filtration process was repeated until the retentate volume was again approximately 20 ml.

FIG. 3 provides a comparison of the volumetric size distribution of the unfiltered microparticle suspension with the 5 micron permeate and the 3 micron retentate. The results, derived from a Malvern Micro particle size analyzer show a stepwise narrowing of the size spectrum toward a specific size range defined by the pore size of the filters used.

EXAMPLE 14

Representative Canine Study of Echogenicity

A 31 kg, thoracotomized male mongrel dog was injected with 1 cc of reconstituted microparticle composition made according to example 4. This was delivered to the circulation through a peripheral venous injection. Triggered harmonic ultrasound imaging (once every beat) of the left ventricle was performed for 9 minutes. A contrast effect could be seen in the myocardium during triggered imaging. Real-time (30 Hz) harmonic ultrasound imaging over the next 4 minutes increased bubble destruction. Left ventricular opacification remained persistent over the 13—minute imaging period. No adverse hemodynamic effects were observed.

In a separate study, 0.1 cc of reconstituted microparticle agent was administered similarly to a thoracotomized male mongrel dog. Triggered harmonic ultrasound imaging was performed for 1 minute, followed by 4 minutes of increased microparticle destruction with real-time imaging. Again, no adverse hemodynamics effects were seen, and left ventricular opacification was apparent and persistent.

EXAMPLE 15

Dye Loading of Albumin Polylactide Microparticles

A lyophilized cake in a 10 ml serum vial, composed of excipient and lactide-containing microparticles prepared in a manner similar to Example 11 was placed into a 50 ml centrifuge tube. Enough isopropyl alcohol was added to cover the cake and it was allowed to soak for 30 seconds. Aqueous Pluronic F68 solution (0.25% w/w) was added to fill the tube. After centrifuging, the supernatant was removed and another rinse performed. A saturated, filtered solution of rhodamine B was added to the microparticles and allowed to soak overnight. Under the microscope, the microparticles appeared filled with dye solution. A dye saturated F68 solution was made to use as a lyophilization excipient. Four ml of the excipient was combined with the approximately 2 ml of microcapsule containing solution and the resulting mixture was split between two 10 ml serum vials. The vials were frozen at −80° C. and lyophilized in a FTS tray dryer. Both vials were purged with perfluorobutane gas by five pump-down purge cycles with a vacuum pump. Observation showed some microparticles that were half full of red solution and half full of gas. There was no obvious leakage of the dye from these microparticles during observation. The microparticles were rinsed with four, 20 ml portions of F68 solution on a vacuum filter. The microparticles were placed in a cuvette, centrifuged, and an initial spectra was taken. The cuvette was sonicated in an ultrasonic bath, centrifuged, and another spectra taken.

| Abs. Initial (553–800) | Abs. Sonicated (553–800) |
|---|---|
| 1.164 | 1.86 |

The higher absorption after sonication indicates that encapsulated dye was released upon insonation of the microparticles.

EXAMPLE 16

Preparation of Wall Modified Albumin Polycaprolactone Microparticles

Albumin coated microcapsules were prepared in a manner similar to example 9 with the exception that 0.20 gm paraffin was also dissolved into the organic solution along with the polycaprolactone and the cyclooctane.

Microscopic inspection of the finished microparticle suspension revealed spherical particles having a morphology and appearance virtually identical to those prepared without the addition of paraffin.

EXAMPLE 17

Dye Loading of Human Serum Albumin Polycaprolactone Microparticles

A lyophilized cake in, a 10 ml serum vial, composed of excipient and paraffin-containing microparticles prepared in accordance with example 16 was placed into a 50 ml centrifuge tube. The cake was covered with methanol and allowed to soak for 30 seconds. The tube was then filled with an aqueous solution of 0.25% (w/w) Pluronic F68, gently mixed, and centrifuged in order to precipitate the now fluid-filled microcapsules. The supernatant was removed and the tubes were again filled with pluronic solution. The microparticles were resuspended by vortexing and again centrifuged. After removing the supernatant solution, two ml of a saturated, filtered solution of brilliant blue G dye in 0.25% (w/w) aqueous F68 was added. The microparticles were allowed to soak for approximately 72 hours. Microscopic examination revealed 90–95% of the microparticles to be filled with dye solution. A lyophilization excipient was prepared. Four ml of the excipient was added to the microparticle solution and mixed by vortexing. Two 10 ml serum vials were filled with 3 ml each of solution and frozen at −80° C. The vials were lyophilized on a FTS flask lyophilizer. Both vials and a portion of deionized water were purged with perfluorobutane for 10 minutes. Both vials were reconstituted with deionized water and rinsed with two 40 ml portions of 0.25% (w/w) F68 solution on a vacuum filter. The resulting microparticle solution was split into two 3 ml portions. One portion was sonicated in an ultrasonic bath to rupture the bubbles. Both portions were diluted 1/10 with F63 solution and placed into UV-visible cuvettes. The cuvettes were centrifuged and a visible spectra was taken.

| Sonicated | 0.193 |
|---|---|
| Non-sonicated | 0.136 |

The higher absorption after sonication indicates that encapsulated dye was released upon insonation of the microcapsules.

EXAMPLE 18

Acoustic Resonance of Microparticles

To demonstrate a method of acoustically tuning the microparticle construct, microparticles prepared in accordance with the procedures described in examples 9 and 16 were reconstituted with deionized water and compared for their acoustic properties using procedures described as follows:

Two matched 5 MHz transducers were placed in a tank filled with degassed water facing one another. Water depth was approximately 3 inches. The transducers, one an emitter and the other a receiver, were positioned 6 inches apart to maximize the received signals. A 2 inch diameter, 2 cm wide circular chamber was placed between the two transducers with the mid chamber position at 3 inches from the emitter. The two circular faces of the chamber were covered with 3 mil polyethylene film and the chamber was then filled with degassed water. Sound waves readily propagated from the emitter through the chamber to the receiver. The sound source was set to Gaussian Noise with 10 Volt peak to peak amplitude output from the ultrasound generator. The receiver signal is amplified with a 17 dB preamp and an oscilloscope. The oscilloscope digital electronics can perform Fast Fourier Transforms (FFT) of the received wave forms and display these distributions. After baseline readings were made, test microparticle contrast materials were delivered within the chamber via hypodermic syringe and thoroughly mixed therein by pumping the syringe. During post-test evaluation, the FFT data was converted into the Transfer Function of the test agent.

The Transfer Function (TF) is determined by dividing the bubble transmission spectral data by the spectral data without bubbles, i.e:

$$TF = T(f)_{with\ bubbles} / T(f)_{no\ bubbles}$$

where T(f) is requested by the FFT.

The contrast agent selectively attenuates sound waves depending upon its spectral distribution, i.e. more sound energy is absorbed at or near bubble resonance than off-resonance. Thus the procedure can be used to assess the resonant spectral distribution of the agent.

Data derived from the two agents with nearly identical size distribution but different inner shell thickness were collected on the same day with the same equipment set at the same settings. Everything else was held constant for a variety of agent dosages.

Normalization of the spectra was performed by dividing the spectral array by the minimal value. Thus the peak value becomes unity and when plotted on the same graph it becomes quite easy to differentiate the two graphs. These normalized data are presented in FIG. 4.

Inspection of the results shown in FIG. 4 clearly show that when shell wall compliance is increased, the resonant frequency can be made to shift from 2.3 MHz to 8.9 MHz. Thus, the resonant frequency of an agent can be controlled by controlling the wall composition and thickness.

EXAMPLE 19

Effect of Acoustic Properties on in-vivo Echogenicity

Two air-containing microparticle formulations were evaluated for efficacy in-vivo. One vial of lyophilized microparticles was prepared as described in Examples 1 and 2 (formulation A). A second vial of lyophilized microparticles were prepared in a manner similar to that described in Examples 1 and 2 except that four times the amount of polymer was used, yielding microcapsules with a thick inner wall and hence a higher resonant frequency (formulation B). Both vials were reconstituted immediately prior to use. From particle size analysis, both formulations had a mean microparticle diameter of approximately 4 microns and nearly identical microparticle concentration. In-vitro acoustical characterization showed formulation A to have a resonant frequency near 5 MHz, and formulation B to have a resonant frequency greater than 10 MHz. A 5 MHz transesophageal ultrasound probe was positioned in the esophagus of an anesthetized dog such that a four-chamber view of the heart was obtained. The reconstituted microparticle suspension (4 cc of formulation A) was injected into the femoral vein of the dog. The appearance of the contrast agent was clearly noted in the ultrasound image of the right and left chambers of the heart. Subsequently, 4 cc of the thick walled microparticle suspension (formulation B) was injected into the femoral vein of the dog. While the appearance of the contrast agent was again clearly noted in the ultrasound image of the heart, the contrast effect was substantially diminished when compared to the equivalent volume injection of formulation A. Subsequent injections of dilutions made from formulation A demonstrated a greater than four fold dose effectiveness of formulation A which had a resonant frequency near the center frequency of the ultrasound diagnostic system as compared to formulation B with a greater peak resonant frequency.

What is claimed is:

1. A microparticle composition containing microparticles having diameters within the range of about 1 to 10 microns, said particles having an outer shell and a hollow core, said shell comprising
   an outer layer of a crosslinked biologically compatible amphiphilic material and
   an inner layer comprising an organic solvent soluble biodegradable polymer,
   wherein said inner and outer layers are not covalently linked to each other.

2. A composition according to claim 1, wherein at least a majority of said microparticles have diameters within said range.

3. A composition according to claim 1, wherein said biologically compatible material is blood compatible.

4. A composition according to claim 1, wherein said cores contain a gas.

5. A composition according to claim 1 comprising gas-filled microparticles of a size capable of passing the capillary circulation system of the body, wherein said microparticles are mechanically adjusted to resonate at a predetermined resonant frequency.

6. A composition according to claim 5, wherein said microparticles are selected to resonate at said frequency by particle size adjustment.

7. A composition according to claim 5, wherein said resonant frequency is $\geq 2$ MHz.

8. A composition according to claim 7, wherein said frequency is $\geq 5$ MHz.

9. A composition according to claim 5, wherein the mechanical adjustment is made by selection of wall thickness.

10. A composition according to claim 5, wherein the mechanical adjustment is made by selection of wall material for said microparticles.

11. A composition according to claim 5, wherein the mechanical adjustment is made by the adjustment of the internal pressure within said microparticles.

12. A composition according to claim 5, wherein said resonant frequency is in the range of the transmitted frequencies of a diagnostic body imaging system.

13. A composition according to claim 5, wherein said resonant frequency is a harmonic of a diagnostic body imaging system.

14. A composition according to claim 4, wherein the microparticles are mechanically adjusted to remain stable when exposed to a threshold diagnostic imaging level of power of ultrasound irradiation, and are rupturable when exposed to an increase in said power.

15. A composition according to claim 4, wherein the microparticles are mechanically adjusted to remain stable when exposed to a threshold diagnostic imaging level of power of ultrasound irradiation, and are rupturable when exposed to frequencies near the resonant frequency of the microparticles.

16. A composition according to claim 14 or 15, wherein said microparticles contain blood soluble or insoluble gases.

17. A composition according to claim 14 comprising gas-filled microparticles of a size capable of passing the capillary circulation system of the body and comprising surface targeting moieties for binding to selected tissues.

18. A composition according to claim 14 comprising gas-filled microparticles of a size capable of passing the capillary circulation system of the body and comprising surface conjugated hydrophilic polymers.

19. A composition according to claim 18 wherein said hydrophilic polymers comprise polyethylene glycol.

20. A composition according to claim 18 wherein said hydrophilic polymers comprise polyethylene glycol, polypropylene glycol, their derivatives, or combinations thereof.

21. A composition according to claim 1 wherein said outer layer comprises a chemically-charged outer surface.

22. A composition according to claim 21 wherein said outer surface is PEGylated.

23. A composition according to claim 21 wherein said outer surface is succinylated.

24. A composition according to claim 17, wherein said targeting moieties are selected from the group consisting of antibodies, cell receptors, lectins, selecting, integrins, receptor targets, receptor analogues, and active fragments thereof.

25. A composition according to claim 1, wherein said crosslinked biologically compatible amphilphilic material comprise a protein.

26. A composition according to claim 15, wherein said protein comprises collagen, gelatin, albumin, globulin, or glycosaminoglycan.

27. A composition according to claim 1, wherein said biologically amphiphilic material comprises albumin.

28. A composition according to claim 1, wherein said biologically compatible amphiphilic material comprises a biopolymer.

29. A composition according to claim 1, wherein said polymer comprises polylactide, polyglycolide, or copolymers thereof.

30. A composition according to claim 1, wherein said polymer comprises copolymers of caprolactone with lactic or glycolic acid.

31. A composition according to claim 1, wherein said inner layer is porous.

32. A process for forming multilayer microparticles which are suspendable in a medium suitable for injection, comprising the steps:
   a. forming a mixture of a first aqueous dispersion of a biologically compatible amphiphilic material and mixing with a second solution of a biodegradable polymer wherein said second solution comprises a relatively volatile water-immiscible solvent and a relatively non-volatile water-immiscible non-solvent for said polymer;
   b. emulsifying said mixture from step (a) to form microdroplets having an interior containing said polymer solution and an outer layer comprising said biologically compatible material;
   c. removing said relatively volatile solvent from said microparticles to form an inner layer of said polymer on said biopolymer, wherein said inner layer and said outer layer are not covalently linked to each other;
   d. drying said microparticles to remove said non-solvent and residual water.

33. A process according to claim 32, wherein said step (c) said volatile solvent is removed by evaporation.

34. A process according to claim 32, wherein said step (c) said volatile solvent is removed by dilution.

35. A process according to claim 32 further comprising the step of cross-linking said outer layer.

36. A process according to claim 32, wherein said step (d) is by freeze drying.

37. A process according to claim 32 further comprising the step of loading said microparticles after drying with a gas.

38. A method of generating an image for echogenic inspection comprising the steps of:
   a. introducing into a subject a composition according to claim 4
   b. subjecting said subject to suitable ultrasonic radiation;
   c. detecting ultrasonic radiation reflected, transmitted, resonated and/or frequency and/or amplitude modulated by said microparticles in said subject.

39. A composition according to claim 4, wherein said gas is soluble in blood.

40. A composition according to claim 4, wherein said gas is insoluble in blood.

41. A process according to claim 37, wherein said gas is other than air. than air.

\* \* \* \* \*